United States Patent [19]

Falsetti et al.

[11] Patent Number: 5,445,029
[45] Date of Patent: Aug. 29, 1995

[54] CALIBRATION AND FLAW DETECTION METHOD FOR ULTRASONIC INSPECTION OF ACOUSTICALLY NOISY MATERIALS

[75] Inventors: Robert V. Falsetti, Schenectady; Elizabeth L. Dixon, Delanson, both of N.Y.

[73] Assignee: General Electric Co., Schenectady, N.Y.

[21] Appl. No.: 149,208

[22] Filed: Nov. 8, 1993

[51] Int. Cl.$^6$ ............................................. G01N 29/04
[52] U.S. Cl. ......................................... 73/609; 73/602
[58] Field of Search ................... 364/507; 73/609, 602, 73/596, 627, 575

[56] References Cited

U.S. PATENT DOCUMENTS

4,646,754  3/1987  Seale ..................................... 73/575
5,099,848  3/1992  Parker ................................... 73/575

Primary Examiner—Hezron E. Williams
Assistant Examiner—Christine K. Oda
Attorney, Agent, or Firm—Nixon & Vanderhye

[57] ABSTRACT

A method and apparatus for the ultrasonic inspection of acoustically "noisy" specimens, such as those having intrinsically coarse grain structure (e.g., turbine rotor parts made of superalloy compositions) employs several types of ultrasonic diagnostic measurement techniques, including at least: "Pitch-Catch" analysis and "Pulse-Echo Axial Long-Wave" analysis. When a Pitch-Catch technique is utilized, a "through-transmitted" sound wave is acquired for each specimen tested and used as a calibration standard to normalize ultrasonic inspection test data for that specimen prior to any automated defect/flaw detection and sizing processing. The through transmitted sound wave is also used to equate the amplitude of "indications" (i.e., significant detected ultrasonic reflections) to that of a standardized theoretical reflector of known size (e.g., an equivalent "flat bottom hole" or EFBH reflector) so that the test sensitivity or "size of indications" can be uniquely determined for each specimen on which the test is performed. When a Pulse-Echo technique is utilized, a through-transmitted sound wave is not used (since this technique employs only a single transducer) and inspection data is instead normalized by a "back wall" reflection signal. Once ultrasonic inspection test data is obtained and digitized, a "rolling average" of the data is used to estimate the localized noise level within the material under test. For every transducer pulse data point obtained, a unique signal-to-noise (S/N) ratio is computed. Variations in S/N ratio for the material are measured at each axial slice of material volume inspected. A function of the standard deviation of the S/N values is then used to automatically adjust a detection amplitude threshold to optimize the flaw detection process and minimize false alarms.

20 Claims, 4 Drawing Sheets

CALIBRATION AND FLAW DETECTION METHOD FOR ULTRASONIC INSPECTION OF ACOUSTICALLY NOISY MATERIALS

FIELD OF THE INVENTION

The present invention generally relates to ultrasonic inspection techniques for materials having an intrinsically coarse grain structure which results in anisotropic and nonuniform acoustic properties. More particularly, the invention relates to a calibration technique for "pitch-catch" ultrasonic testing that adjusts for variations in material properties and to an automated flaw/defect detection technique that employs a "floating" detection threshold wherein threshold levels are dynamically adjusted relative to the inherent acoustic noise structure of the specimen under test as opposed to an absolute threshold. Still more particularly, the invention relates to ultrasonic testing of solid disk superalloy forgings used in the construction of large turbine rotors.

BACKGROUND AND SUMMARY OF THE INVENTION

In many environments, the structural integrity of certain critical components of a particular system or apparatus is of the utmost importance in ensuring against future failures. In particular, the construction of large gas turbines imposes strict requirements on performance characteristics and reliability of the parts used. For example, components used in the construction of large gas turbines are typically subjected to great mechanical stresses and must be able to withstand continued exposure to extreme high temperatures, as well as, high velocity corrosive gas streams. One example of such critical components is the rotor of large gas turbines. Conventionally, superalloys (e.g., 40 Ni—15-Cr—Ti—Nb) are utilized as suitable materials for the large solid disk forgings which make up a turbine rotor. To guarantee that the superalloy material quality is high and the structural integrity of rotor forgings is acceptable, special ultrasonic tests were developed to inspect each forging in the plane perpendicular to the highest operating stresses (i.e., the axial-radial plane). In particular, two ultrasonic testing techniques are conventionally used for the nondestructive testing of turbine rotor disk forgings near the highly stressed bore region: (1) a "Pitch-Catch" technique using two ultrasonic transducers, and, (2) a "Pulse-Echo Axial LongWave" technique that uses only a single transducer.

Ultrasonic Pitch-Catch testing per se is known and is commonly used to inspect machine components for material defects oriented perpendicular to the testing surfaces. However, in the past, these tests have been performed either uncalibrated (where simply the presence, but not the size of a defect is important), or a calibration was performed by using external blocks of material containing machined reflectors of a known dimension. Calibration references of this sort for conventional Pitch-Catch testing are listed in the nondestructive testing handbook and other reference tests, such as *Krautkramer's Ultrasonic Testing of Materials*. Unfortunately, these attempts at calibration, or the lack of calibration fail to compensate Pitch-Catch inspection data for variations in acoustic properties that are inherently present in many superalloy materials. More specifically, many superalloys are anisotropic and present nonuniform acoustic properties as a result of an intrinsically coarse grain structure. Consequently, such variations in the acoustic properties of superalloys affect the Pitch-Catch sensitivity, as well as the ability to estimate the size of a detected defect from its reflected signal amplitude.

A further disadvantage of not calibrating a Pitch-Catch test procedure is that no size information is provided following detection of a defect. In addition, the sensitivity of the test would be unknown. Without some estimate of defect dimensions, structural analysis cannot be accurately performed to determine the severity of such a defect on the mechanical performance and reliability of the particular component part.

In the alternative, if some external material is used for calibration, the relationship established in the external reference will not be applicable to the particular forging specimen under test. This is because due to their highly nonuniform properties, no two superalloy forgings are alike. In fact, acoustic properties within the same forging may vary considerably. Therefore, an external calibration standard, even using similar material, would fail to completely characterize the specific forging specimen being tested. In addition, many combinations of forging sizes and calibration reference reflectors would be required to address all components of a particular product line. Moreover, the effective changes in engineering requirements on test sensitivities would be difficult or impossible to predict.

In accordance with the present invention, a calibration technique is provided for conventional Pitch-Catch ultrasonic testing procedures that adjusts for variations in material ultrasonic test properties. More specifically, in accordance with the calibration technique of the present invention, "through-transmitted" sound waves are collected prior to the Pitch-Catch diagnostics on the forging and used to normalize all subsequently collected Pitch-Catch inspection data. In addition, measured amplitudes of potential fault indications ("indication amplitudes") are equated to a known reference defect (e.g., an equivalent flat bottom hole) by a particular relationship (discussed further herein) based on the through transmitted sound wave, component thickness and the ultrasonic test specimen/material characteristics.

Since the through-transmitted sound wave is affected by the material acoustic properties in the same way that the inspection test data is affected, it can be used to normalize the inspection data prior to automated defect detection or sizing. In addition, using the through-transmitted sound wave to equate the amplitude of defect indications to a known sonic reflection standard, such as an FBH reflector, allows the current test sensitivity (size of indications) to be determined uniquely for each Pitch-Catch test conducted. Using a through-transmitted sound wave in this manner provides a means to uniquely compensate for variations in acoustic properties from forging to forging as well as within any given forging.

In addition to the specific above-mentioned problems inherent to Pitch-Catch diagnostics, prior art ultrasonic inspection techniques of all types prove difficult (if not impossible) to adjust flaw/defect detection threshold levels to always obtain an optimized sensitivity for testing acoustically noisy materials. Ultrasonic inspection systems conventionally rely on an expected echo-dynamic pattern associated with the reflection of ultrasound from a defect as the sound beam traverses it. The prior art ultrasonic flaw/defect conventional flaw detection and recognition methods as employed in Pitch- Catch, Pulse-Echo or other diagnostic techniques, in general, either use a fixed predetermined amplitude as a defect recognition threshold, or use no threshold at all. In systems using fixed thresholds, the threshold is adjusted to a level that is determined by the test system operator based on a known reflector size or set to a level slightly higher than an approximation of a general (average) noise level observed in the material.

Consequently, when testing acoustically noisy components like turbine rotor disks, if the detection criterion is based solely on the expected echo-dynamic pattern from a flaw/defect, and no thresholds are used, an abnormally high number of false defect indications are encountered as a result of the nonuniform distribution of acoustic noise within the component material. This is due to the fact that acoustic noise patterns in various superalloy materials used in turbine rotors are coherent enough (i.e., have the proper echo-dynamic characteristics) to actually appear as real defect indications. Accordingly, the echo-dynamic characteristics of such materials make the use of amplitude detection thresholds absolutely necessary when testing turbine rotor forgings of other parts which use superalloy materials. However, because the noise structure in rotor forgings is typically nonuniform, not only between two separate forgings but within single forgings as well, selection of an absolute threshold value is not feasible. It would, invariably, require the setting of some arbitrary threshold quite high above observed noise peaks to eliminate false alarms. Obviously, such a setting does not provide optimum test sensitivity. Accordingly, for the purpose of testing turbine rotor forgings and other components made of superalloys or other acoustically noisy materials, it would be highly desirable to have a testing system which could dynamically optimize the test sensitivity. An improved automatic flaw/defect scanning and detection technique in accordance with the present invention solves this problem by providing the capability to dynamically adjust the flaw/defect detection threshold level so as to instantly and automatically respond to changing noise patterns. Moreover, the improved technique is readily applicable to both Pitch-Catch and Pulse-Echo diagnostics as well as other techniques, as will be recognized by one of ordinary skill in the art upon reading the following description of the invention.

In accordance with the improved automatic flaw/defect scanning and detection technique of the present invention, a "rolling average" of digital ultrasonic inspection (measurement) data is used to estimate the "local" noise level and compute a unique signal-to-noise (S/N) ratio for every data point (i.e., transducer pulse) generated. Variations in the S/N ratio for the material are measured at each axial slice of material volume inspected. A predetermined function of the standard deviation of the calculated S/N ratio values is then used to continuously adjust the detection amplitude threshold to dynamically optimize the defect detection criterion and minimize false alarms. This predetermined detection threshold function, as discussed in greater detail further herein, can also be varied to accommodate the particular type of test being performed (i. e., pitch-catch, axial long-wave, etc. ). Subsequent additional processing of sequential S/N values is then performed to determine whether a recorded internal reflection, i.e. , a "target," meets a particular predetermined criteria for a defect indication. The echo-dynamic behavior of the S/N values must, therefore, correspond to a dynamically custom-tailored "expected" response from a target to be reported as a defect indication. Thus, the automatic flaw/defect detection technique in accordance with the present invention provides increased defect detection sensitivity over conventional methods and continuous automatic adjustment of the detection threshold based on the particular intrinsic material properties of the part being inspected.

BRIEF DESCRIPTION OF THE DRAWINGS

These and other features and advantages of the present invention will become more completely understood by referring to the following detailed description of presently preferred exemplary embodiments in conjunction with the FIGURES in which like reference numerals refer to like elements throughout.

DETAILED DESCRIPTION OF THE DRAWINGS

In the following description, for purposes of explanation and not limitation, specific details are set forth, such as particular system components, equipment, diagnostic techniques, exemplary computer program flow steps, etc., in order to provide a thorough understanding of the present invention. However, it will be apparent to one skilled in the art that the present invention may be practiced in other embodiments that depart from these specific details. In other instances, detailed descriptions of well known methods and programming procedures, devices, and circuits are omitted so not to obscure the description of the present invention with unnecessary detail.

Figure 1:
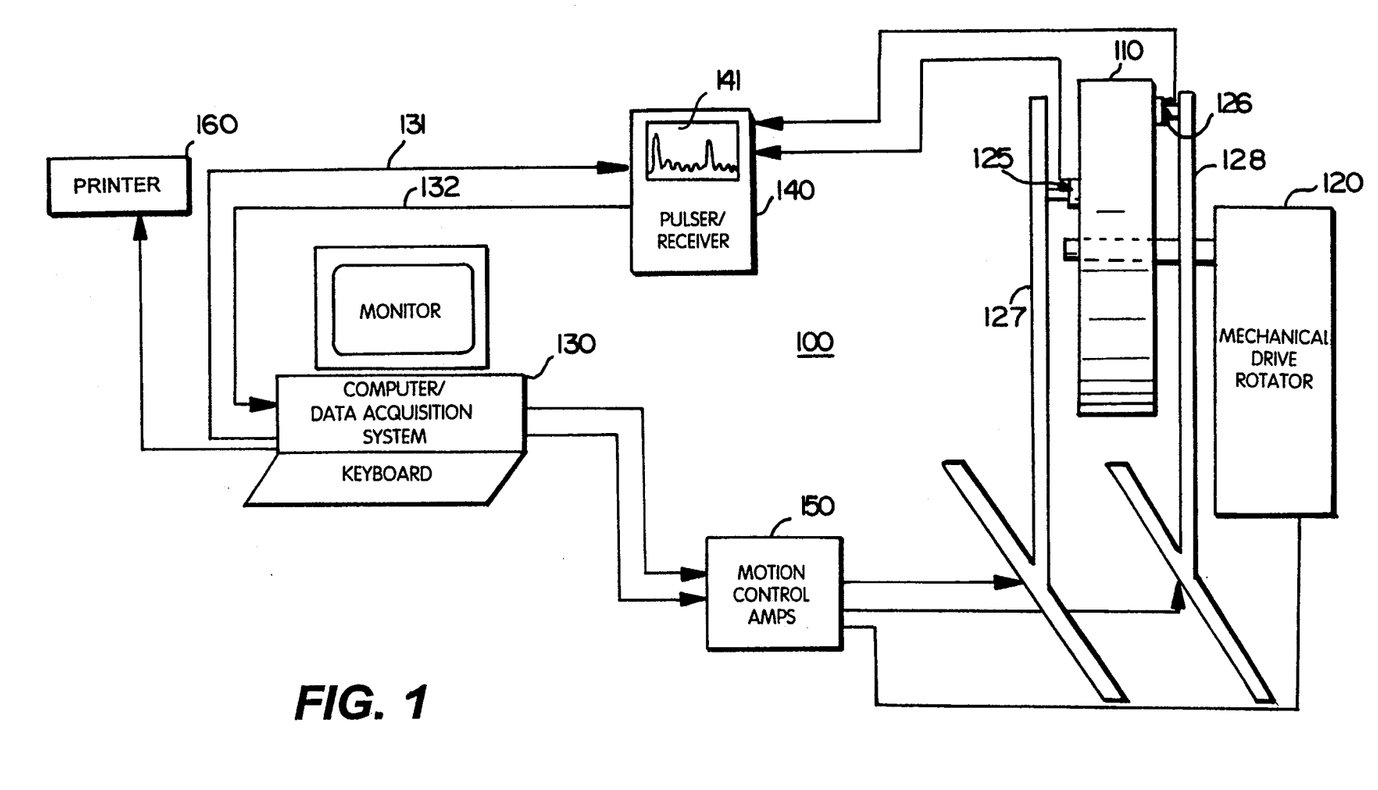
FIG. 1 is a schematic block diagram of an ultrasonic inspection system for the automated nondestructive testing of turbine rotor disk forgings in accordance with a preferred exemplary embodiment of the present invention.
Figure 2A:
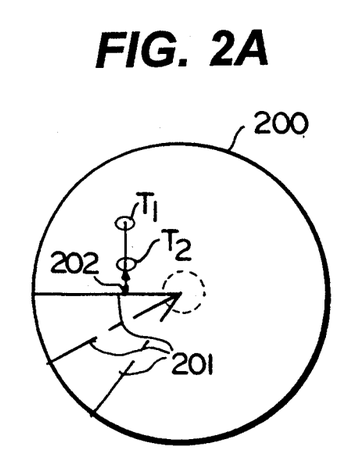
FIGS. 2A and 2B are, respectively, front and side schematic views illustrating a Pitch-Catch test set-up for performing ultrasonic measurement on a turbine disk forging.
Figure 2B:
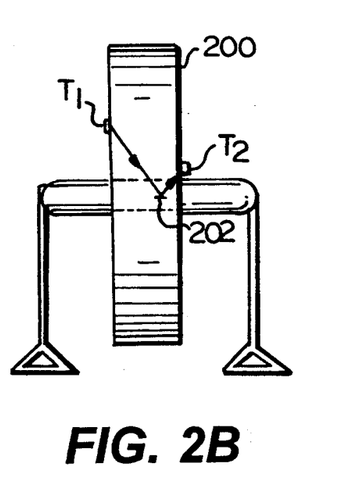

Referring to FIG. 1, a schematic diagram of an exemplary ultrasonic testing and measurement system 100 for the inspection of gas turbine rotor parts is shown. A turbine disk rotor forging 110 under test is rotated on a mechanical drive system 120. Inspection data is acquired in the form of ultrasonic echoes gated from transducer units 125 and 126 via a logarithmic ultrasonic pulser/receiver instrument 140 and digitally processed by computer/data acquisition system 130 with amplitude and polarity information being preserved. The data acquisition system used in practicing the present invention may be, for example, a conventional personal computer system with keyboard, display and monitor (equipped, for example, with servo motion control boards, such as a Galil 3-Access 600 series motion control board, and an analog-to-digital converter card, such as a Sonix 8100 A/D board). Pulser/receiver 140 (for example, a GE Amput pulser/receiver instrument) provides excitation signals to transducer units 125, 126 and sends received (detected) ultrasonic echo signals from transducer units 125, 126 to an analog-to-digital convertor (not shown) within data acquisition system 130. Pulser/receiver 140 may also be provided with a CRT (141) for displaying ultrasonic signals picked up by transducers 125, 126.

Trigger input line 131 provides pulser/receiver 140 with timing signals from computer/data acquisition system 130. Received ultrasonic signals are provided to the data acquisition system via line 132. An analog-to-digital (A/D) converter within the data acquisition system digitizes all analog measurement signals provided by pulser/receiver 140. Transducers 125,126 are supported on respective probe support towers 127,128, which provide dual axes (x-y) scanning movement capability. Mechanical drive rotator 120 and support tower dual axes drive servos (not shown) are controlled by data acquisition system 130 via motion control amplifiers 150. A printer, 160, or other output and storage devices may also be connected to computer/data acquisition system 130.

Although ultrasonic testing system 100 is configured specifically for testing gas turbine disk forgings rotated on a mechanical drive system, the transducers, transducer housing/coupling support mechanism and scanning arrangements may be modified to accommodate different components, testing procedures and applications. For example, certain testing procedures require a pair of transducers (e.g., a Pitch-Catch test), while other procedures require the use of only a single transducer (e.g., a Pulse-Echo Axial Long-Wave test).

Figure 3A:
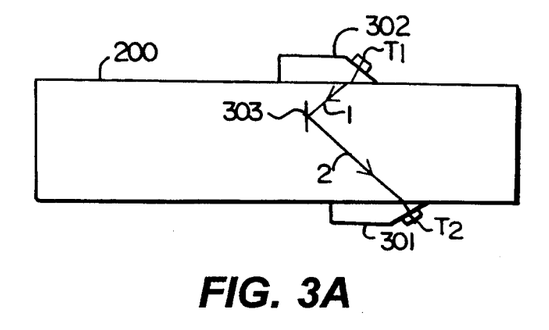
FIG. 3A is a diagrammatic illustration of the orientation of ultrasonic transducer units on a rotor disk forging during a Pitch-Catch test procedure.
Figure 3B:
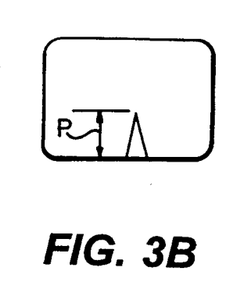
FIG. 3B is an illustration of a CRT display showing the peak amplitude of an exemplary defect indication obtained using the transducer configuration shown in FIG. 3A.

Referring now to the schematic views shown in FIGS. 2A–3B, the basic set-up for a Pitch-Catch test procedure is discussed. Briefly, two "angled beam" transducer units T1 and T2 (i.e., a transducer in a predetermined angled acoustic coupler/housing) are placed on opposite side surfaces of rotor disk forging 200. Transducers T1 and T2 are operated in a transmit-receive mode and directed toward an axial-radial plane of the forging. Forging disk 200 is then rotated by a mechanical drive mechanism and as the forging rotates, its axial-radial planes 201 pass through the beam path 202 intersection creating an "inspection volume." (For example, after a single rotation, a toroid of material has been inspected.) Transducer units T1 and T2 are swept radially in unison to complete the inspection of one axial slice (i.e., plane) of material. To complete the process, transducer units T1 and T2 are also moved relative to each other so that the beam path intersection 202 moves axially across the forging. FIG. 3A shows the orientation of the angled beam transducer units (301 and 302) positioned on opposite side surfaces of disk rotor forging 200 and illustrates the sound path legs (1 and 2) of an exemplary ultrasonic beam incident upon a detected defect (or "target") 303. FIG. 3B illustrates an exemplary pulser/receiver unit CRT display of the peak amplitude, P, of defect/indication 303 in FIG. 3A.

Figure 4A:
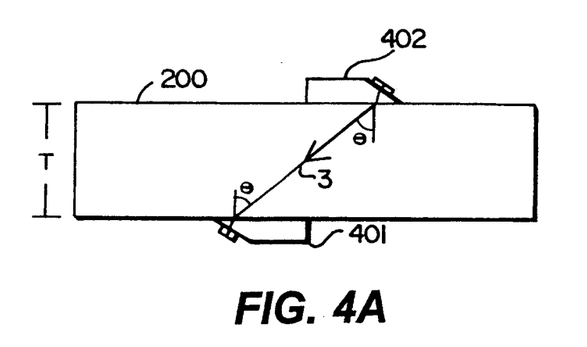
FIG. 4A is a diagrammatic illustration of the orientation of transducers on a turbine rotor disk forging for obtaining through-transmitted sound wave data for normalization of Pitch-Catch test measurement data.
Figure 4B:
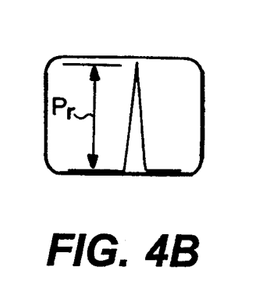
FIG. 4B is an illustration of a CRT display showing the peak amplitude of a reference through-transmitted sound wave signal obtained using the transducer configuration shown in FIG. 4A.

Referring now to FIG. 4A, an improved calibration method for Pitch-Catch testing in accordance with the present invention is accomplished by rotating one of the transducer units by 180° and displacing it by approximately the forging thickness, T, so that both transducers T1 and T2 are aiming directly at each other. The ultrasonic beam path 3 passes uninterrupted from transducer unit 402 to transducer unit 401 and peak signal obtained is referred to as the "through transmitted sound wave." The placement of units 401 and 402 is adjusted to maximize the amplitude of the through-transmitted sound wave. Angle $\theta$ is measured and used in defect detection "sizing equation" (discussed below) along with the maximize amplitude of the through-transmitted sound wave. FIG. 4B illustrates an exemplary pulser/receiver CRT display of the peak reference amplitude, $P_r$, of the through-transmitted wave traveled along the path (3) in FIG. 4A.

Although the maximum sound pressure relative to a defect is typically obtained at 45°, in accordance with a presently preferred exemplary embodiment of the present invention, a slightly lower angle of 40° is used because it shortens the sound path distance within the forging, and hence lowers the attenuation of sound between the search units. Prior to performing the actual Pitch-Catch inspection, a unique through-transmitted sound wave (i.e., the thru-wall reference signal) is obtained at many "reference" locations on the forging. The through-transmitted wave reference signal obtained at a location nearest to each Pitch-Catch test data point is then divided into the Pitch-Catch data to normalize it prior to any post-processing.

Moreover, since certain superalloy materials are considerably bandpass sensitive, the Fourier Transform of the thru-wall reference signal is computed and compared to the search unit's unfiltered bandpass. Before testing, the filtered and unfiltered bandpasses are matched as closely as possible in order to maximize the test sensitivity. In addition, a "scan plan" is determined prior to testing based on the forging dimensions and transducer unit frequency. The "intersection beam" dimensions are calculated by conventional techniques for each location in the forging and the scan plan is controlled to produce a near uniform sound field within the inspection volume.

In accordance with the present invention, a defect "sizing equation" is used to determine an equivalent flat bottom hole (EFBH) reflector diameter, Dr, of a defect indication based on parameters such as the peak amplitude of reflected sound, the amplitude of the thru-wall reference signal at the location of the indication, and other known or conventionally calculated quantities. In the present invention, $D_f$ is calculated using the sizing equation, EQU. (1), immediately below, by computer/data acquisition system 130:

$$D_f = \sqrt{\frac{4Pvz(T-z)}{\pi P_r T \sin(\theta)\cos(\theta)}}$$ Equ. (1)

where

P = peak amplitude of the indication $P_r$ = amplitude of thru-wall reference signal at location of the indication v = shear wave velocity of sound in the material z = distance of the indication from the nearest surface of the forging (known from beam intersection point calculations)

T = axial thickness of the forging f = measured frequency of the thru-wall reference signal θ measured intercept angle between the search units In addition, to account for the effects of the nonlinear on-axis sound pressure distribution near the transducer (i.e., "near field" effects), a correction is applied to the EFBH diameter determined above. The corrected diameter, $D_{fc}$, is calculated by computer/data acquisition system 130 using EQUATION (2) immediately below (subscript references [1,2,3] represent the sound path legs identified in FIGS. 3A and 4A):

$$D_{fc} = D_f \times \sqrt{\frac{C_1 \times C_2}{C_3}}$$ Equ. (2)

where $C_n = 2.1/x$  for $x < 1$ $C_n = 3.067 - 1.15x + 0.159x^2$  for $1 \leq x \leq 3$ $C_n = 1$  for $x > 3$ $n = [1,2,3]$ and where $$\begin{cases} x = 8vz/D_t^2 f\cos(\theta) & \text{for } n = 1 \\ x = 8v(T-z)/D_t^2 f\cos(\theta) & \text{for } n = 2 \\ x = 8vT/D_t^2 f\cos(\theta) & \text{for } n = 3 \end{cases}$$

and $D_t$ = transducer diameter

T = axial thickness of the forging v = shear wave velocity of sound in the material z = distance of the indication from the nearest surface of the forging θ = measured intercept angle between the transducer units As explained above, in accordance with the present invention, the Pitch-Catch data is normalized by the amplitude of thru-wall reference signals to adjust for acoustic variations in components under test resulting from, for example, the grain structure of the material or surface condition of the part. However, for a "Pulse-Echo" Axial Long-Wave type diagnosis, only a single transducer is used and, prior to any subsequent processing, the acquired data is normalized by an internal reference reflection obtained from the rotor disk forging side wall opposite the transducer (i.e., a "back wall" reflection).

An automatic flaw detection technique for ultrasonic inspection system 100 that has a dynamically adjusting detection threshold capability in accordance with the present invention, and is applicable to both Pitch-Catch and Pulse-Echo diagnoses as well as other conventional techniques, is now discussed with respect to FIGS. 5A–6B.

Figure 5A:
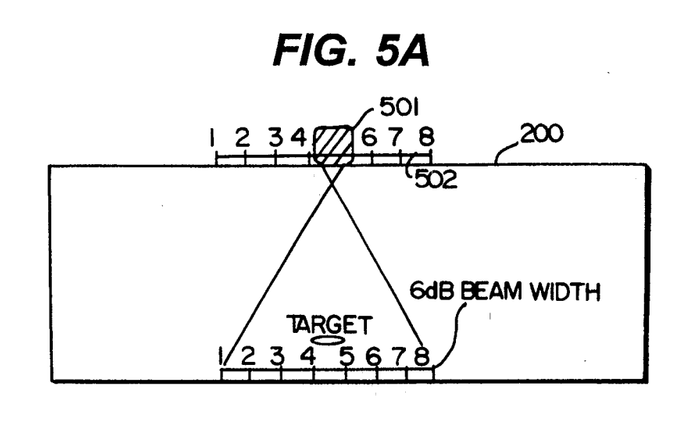
FIG. 5A is a diagrammatic illustration of a single transducer scanning arrangement of a turbine rotor disk forging.
Figure 5B:
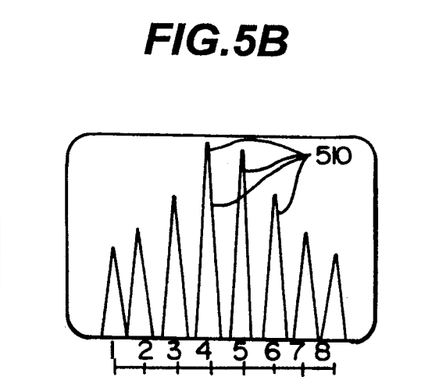
FIG. 5B is an illustration of a CRT display showing an exemplary echo-dynamic response pattern of a defect during eight consecutive ultrasonic pulses for the scanning arrangement of FIG. 5A.

Referring first to FIG. 5A, a diagram of a generalized test set-up for ultrasonic diagnosis of a turbine rotor disk forging (200) in accordance with the present invention is illustrated. Although FIG. 5A depicts only the single transducer arrangement conventionally associated with a Pulse-Echo diagnosis, the scanning/pulsing technique basically illustrated therein and described below is applicable to Pitch-Catch and other types of ultrasonic diagnosis as well. During data acquisition scanning, ultrasonic transducer 501 is pulsed at a repetition frequency sufficient to produce eight pulses as its 6dB sound beam-width width traverses any given point in the material as indicated by scale 502. As illustrated in FIG. 5B, which shows an exemplary pulser/receiver CRT display of a defect (target) scanned during eight consecutive ultrasonic pulses each having a 6 dB beam-waist intersection width, at the defect a preferred scanning/pulsing arrangement results in at least eight responses (510) from any flaw/defect. The 6 dB sound beam-waist width position is chosen so that the echo-dynamic response pattern obtained will approximately rise and fall by a factor of two, as illustrated by the respective amplitudes of the eight pulse waveforms shown in FIG. 5B.

Figure 6A:
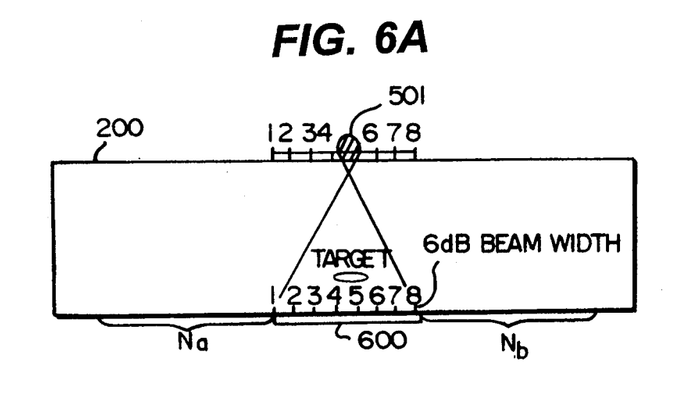
FIG. 6A is a diagrammatic illustration of an ultrasonic scanning arrangement for accomplishing S/N averaging over an arcuate region of a turbine rotor disk forging.
Figure 6B:
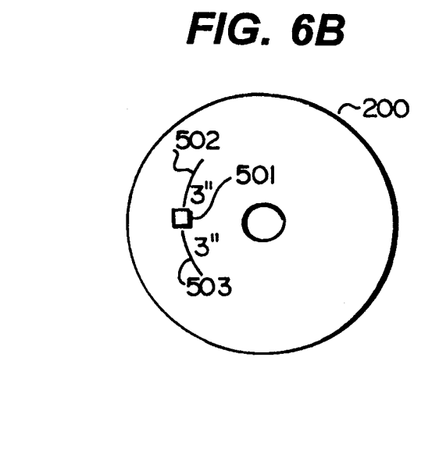
FIG. 6B is a schematic diagram of a side view of a disk rotor forging illustrating the arcuate distance on either side of a transducer over which a localized average noise level is obtained for each measurement.

For each transducer pulse, a "rolling average" is computed to calculate the local noise level over approximately a six-inch arc along the arcuate scan direction (illustrated in FIG. 6B). As shown in FIG. 6A, the beam intersection width (600) is left out of averaged areas, $N_a$ and $N_b$, so that the insonified target does not interfere with the noise calculation. In FIG. 6B, arcs 502 and 503 represent two separate arcuate data regions (each is approximately 3") over which local noise is averaged on either side of transducer unit 501. Each increment in the direction of the sound wave propagation, called a "plane of dam," is treated independently in these rolling average noise calculations. This rolling average calculation of data also acts as an effective filter for changes in the scan responses due to, for example, the initial ultrasonic pulse, attenuation decay and standing waves. For each digital point (or pulse of the transducer), defined as i, the local noise level, Ni, is calculated by computer/data acquisition system 130 using EQUATION (3) immediately below from the signal amplitude, S., acquired at each measurement point in the inspection:

$$N_i = \frac{\sum_{j=i-(b/2)-3''}^{i-(b/2)} S_j + \sum_{j=i+(b/2)}^{i+(b/2)+3''} S_j}{n}$$ Equ. 3 where b = 6 dB beam width in the scan direction and n = total number of data points in the 6" average Next, a signal-to-noise ratio for each point $[S/N]_i$, is calculated by dividing the signal amplitude at point i, $S_i$, by the local noise level $N_i$. In this manner every digital data point acquired within a given data plane is converted into a S/N value (see FIG. 6A).

The detection threshold for the plane is then computed as a function of the standard deviation, $\sigma$, of the S/N values. The standard deviation, $\sigma$, is computed by computer/data acquisition system 130 using the following equation:

$$\sigma = \sqrt{\frac{n\Sigma\left(\frac{S}{N}\right) - \left(\Sigma\frac{S}{N}\right)n}{n(n-1)}} \quad \text{Equ. (4)}$$

where n=total number of data points in plane Exemplary detection thresholds for each type of diagnosis are set as follows:

For:

Pitch-Catch Test: Detection Threshold = $1 + 2\sigma$
Axial Long Wave Test Detection Threshold = $1.3x(1 + 2\sigma)$ Near Field Zone
= $1.1x(1 + 2\sigma)$ Elsewhere Based on the expected "persistence" (i.e., pulses per beam width) of a valid target, a detection is considered if eight consecutive values of S/N equal or exceed the detection threshold.

An indication threshold, equal to twice the detection threshold, is used to ensure that the detection has the expected echo-dynamic pattern of a valid target. Because the transducer was pulsed eight times per 6 dB beam width, at least one point in the detected S/N group must equal or exceed the indication threshold.

Procedural steps for implementing a Pitch-Catch Ultrasonic diagnostic test in accordance with the present invention, using an ultrasonic inspection system as depicted in FIG. 1 and including exemplary computer program flow steps, are set forth immediately below:

Step 1: Position the transducers on the part to obtain a through-signal. Set signal sensitivity by adjusting the gain. Using this through-signal, acquire a reference set of data by pulsing once per degree in concentric revolutions spaced one inch apart over the inspectable portion of the part.

Step 2: Plan a scan of the part so that data will be acquired in a Pitch-Catch manner. (The targeted position of a pulse will fall on an axial plane. Axial planes are spaced on 3 dbK beam width apart. The target positions will, thus, be arranged in concentric revolutions within the plane spaced one 3 dbK beam width apart. Along a revolution, the "targets" will be one-eight of a 6 dbK beam width apart).

Step 3: Acquire the axial planes of Pitch-Catch data. For each pulse a single peak is obtained.

Step 4: Determine the Maximum and Average Signal-to-Noise Ratio for each axial plane of data in the following manner:

Loop over each axial plane.
  Initialize the number of non-noise spike peaks in the plane to zero.
  Initialize the Sum of S/N ratios for the plane to zero.
  Initialize the Maximum S/N ratio for the plane to zero.
  Loop over each revolution of a plane.
    Loop over each peak of a revolution of a plane.
      Normalize the peak using the nearest reference
      Validate that the normalized peak is not a noise spike—a spike will be greater than three times the normalized amplitudes of the peaks on either side-ignore any noise spikes
      Add valid peaks to the number of peaks in a plane.
      Using the running average approach, determine the local noise of this peak (Ni)
      Calculate the signal-to-noise ratio for this peak.
      Compare with the Maximum Signal-to-Noise Ratio for the plane so far and if this peak's exceeds, save the new maximum.
      Add the S/N ratio for this peak to the Sum of S/N ratios for this plane.
    End Loop over each peak of revolution of plane.
  End Loop over each revolution of plane.
  Calculate the Average Signal-to-Noise Ratio for this plane using the Sum of Signal-to-Noise Ratios for this plane and the number of valid peaks in the plane. The Average Signal-to-Noise Ratio is, as expected, essentially equal to 1.0.
End loop over each axial plane.

Step 5: For each axial plane calculate the Noise Threshold for the plane. This Noise Threshold is equal to the Average Signal-to-Noise Ratio for the plane plus two standard deviations.

Step 6: Evaluate each axial plane of data looking for flaw indications in the following manner.

Loop over each axial plane.
  Skip any plane whose Maximum Signal-to-Noise Ratio for that plane is less than twice the Noise Threshold for that plane.
  For a plane not skipped, loop over revolutions of the plane
    Loop over normalized peaks of revolution of plane
      Using the running average approach determine the local noise of this peak.
      Calculate the S/N ratio for this peak.
      For any peak whose S/N ratio is above the Noise Threshold for the plane, build a set of peaks along the revolution. If the set of peaks builds up to equal or exceed the 6 dbk beam width, then declare this group as part of an indication and send it into a nearness algorithm which builds up indications.
    End loop over normalized peaks of revolution of plane.
  Loop over each axial plane.

Step 7: As the nearness algorithm building groups of peaks determines that the set for an indication is closed, the indications are given a flaw size based upon the location of the indication. This flaw size is reported with the location within the part.

Procedural steps for implementing a Pulse-Echo Axial Long-Wave ultrasonic diagnostic test in accordance with the present invention, using an ultrasonic inspection system as depicted in FIG. 1 and including exemplary computer program flow steps, are set forth immediately below:

Step 1: Position the transducer on the part to obtain a Pulse-Echo signal; Set signal sensitivity by adjusting the gain.

Step 2: Plan a scan of the part so that waveforms of data will be acquired in a Pulse-Echo manner. (The waveforms are to be collected by scanning in concentric revolutions on the surface of the inspectable portion of the part. The revolutions are to be spaced twice the near field beam width apart and the ultrasonic pulses are also to be spaced that same distance apart along a revolution. The waveform should be acquired at 25 MHz sampling rate to one inch beyond the backwall reflection of the part. The peak at the backwall is saved for every pulse as a reference through signal for that pulse. The waveform is then compressed into bins each representing an axial quarter inch of depth. Only the peak within each bin of the waveform is saved. A zoned approach is then applied to the waveform. The bins of the waveform are each associated with zone. A zone is referenced to its distance from the transducer and its relationship with the near field zone of the transducer. Each zone has an expected pulse interval for an indication to be valid. It is only necessary to save enough waveform zones within a location on the part to meet the expected pulse interval within the beam spread. Based on the location of the transducer the saved zones of this waveform pulse are determined. Every bin within the near field zone is saved on every pulse. For instance, the expected pulse interval within this zone is "two". Accordingly, it is necessary only to recognize two pulses with normalized peaks within the near field zone having a signal-to-noise ratio above the noise threshold to call an "indication" at that location).

Step 3: Acquire the set of compressed zoned waveforms in the Pulse-Echo manner.

Step 4: Break apart the compressed zoned waveforms into axial planes of data similar to that which would have been collected during the Pitch-Catch test. Each plane of data is spaced a quarter inch apart. The spacing of revolutions and the peaks along a revolution are uniform as the result of the design of the zoning algorithm. The backwall reference for each peak in a plane is known.

From this step on (i.e., once the data has been broken up into axial planes) the evaluation of the data is now very similar to the method used on the Pitch-Catch test. One difference is that three levels of Noise Threshold are calculated; a Low noise threshold using two standard deviations as in the Pitch-Catch test, a Mid noise threshold using three standard deviations and a Hi noise threshold using four standard deviations. The noise threshold calculation is then based on the zone that the plane lies in. A multiplier of 1.3 times is applied to the near field zone planes and a multiplier of 1.1 for all other zones. Another variation lies in the algorithm for testing the association of points to form an indication group. There are three classes of sets, each using one of the levels of noise threshold, and a different association criteria. (Noise spikes are typically not a problem in this test).

Step 5: Determine the Maximum and Average S/N ratio for each axial plane of data in the following manner:
Loop over each axial plane.
Initialize the number of non-noise spike peaks in the plane to zero.
Initialize the Sum of S/N ratios for the plane to zero.
Initialize the Maximum S/N ratio for the plane to zero.
Loop over each revolution of a plane.
Loop over each peak of a revolution of a plane.
Normalize the peak using the backwall reference
Add this peak to the number of peaks in a plane.
Using the running average approach, determine the local noise of this peak (Ni)
Calculate the S/N ratio for this peak.
Compare with the Maximum S/N ratio for the plane so far and if this peak's exceeds, save the new maximum.
Add the S/N ratio for this peak to the Sum of S/N ratios for this plane.
End Loop over each revolution of plane.
Calculate the Average S/N ratio for this plane using the Sum of S/N ratios for this plane and the number of valid peaks in the plane. the Average S/N ratio is, as expected, essentially equal to 1.0.
End loop over each axial plane.

Step 6: For each axial plane, calculate three Noise Thresholds for the plane. The Lo Noise Threshold is equal to the Average S/N Ratio for the plane plus two standard deviations. the Mid Noise Threshold uses three standard deviations and the Hi Noise Threshold uses four standard deviations. The zone which the axial plane belongs to then applies a multiplier of 1.3 for the near field zone and 1.1 for all other zones.

Step 7: Evaluate each axial plane of data looking for flaw indications in the following manner:
Loop over each axial plane.
Skip any plane whose Maximum S/N Ratio for that plane is less than the Lo Noise Threshold for that plane.
For a plane not skipped, loop over revolutions of the plane
Loop over normalized peaks of revolution of plane
Using the running average approach determine the local noise of this peak.
Calculate the S/N Ratio for this peak.
For any peak whose S/N Ratio is above the Noise Threshold levels for the plane, build a set of peaks along the revolution, taking neighboring revolutions into consideration. If the set of peaks builds up to either equal or exceed the 6 dbk beam width and the noise level based neighboring revolution criteria are met, then declare this group as part of an indication and send it into a nearness algorithm which builds up indications.
End Loop over normalized peaks of revolution of plane.
Loop over revolutions of the plane.
Loop over each axial plane.

Step 8: As the nearness algorithm building groups of peaks determines that the set for an indication is closed, the indications are given a flaw size based upon the location of the indication. This flaw size is reported with the location within the part.

While the present invention has been described and illustrated in connection with what is presently considered to be the most practical and preferred embodiments, it should be understood that the present invention is not limited thereto since modifications may be made by persons skilled in the art. The present invention contemplates any and all modifications and equivalents that fall within the spirit and scope of the underlying invention disclosed and claimed herein.

What is claimed is:

1. In a nondestructive testing system for performing ultrasonic inspections, including a processor for controlling the positioning of at least one ultrasonic transducer element with respect to a surface of a specimen under test, acquiring, digitizing and preserving ultrasonic measurement data produced at least in part from internal scattering of ultrasonics signals in the specimen, and performing calculations based on said data, a method for dynamic automatic adjustment of a flaw/defect detection threshold, comprising the steps of:

(a) scanning a surface of a specimen under test in a predetermined pattern with at least one transducer and operating at least one transducer that is used for said scanning to acquire groups of ultrasonic measurement signal data corresponding to a plurality of ultrasonic test data points arranged within distinct planes, said distinct planes defined substantially parallel to the scanned surface of said specimen;

(b) calculating a unique signal-to-noise (S/N) ratio value corresponding to each test point of said plurality of ultrasonic test data points in a particular plane of said distinct planes based on a rolling average of signal levels measured over an area localized about each of said plurality of ultrasonic test data points acquired in step (a); and (c) setting a flaw/defect detection threshold level for said particular plane in said specimen based on a predetermined function of a standard deviation value of all S/N values calculated for said particular plane in step (b).

2. The method for dynamic adjustment of a flaw/defect detection threshold according to claim 1, wherein said scanning step is performed at a predetermined transducer velocity with respect to the specimen surface and using a corresponding ultrasonic pulse repetition rate that insures a plurality of ultrasonic pulse echo responses for each test point of said plurality of ultrasonic test data points scanned in said specimen.

3. The method for dynamic adjustment of a flaw/defect detection threshold according to claim 2, wherein said ultrasonic pulse repetition rate results in at least eight pulses for each test point of said plurality of ultrasonic test data points scanned.

4. The method for dynamic adjustment of a flaw/defect detection threshold according to claim 1, wherein during said scanning in step (a), at least one transducer is operated to provide ultrasonic pulses at a repetition rate sufficient to produce a plurality of ultrasonic pulse echo responses from a flaw/defect such that an echo-dynamic response pattern of echo response amplitudes obtained during scanning of a flaw/defect will comprise values ranging in magnitude from least to greatest by approximately a factor of two.

5. The method for dynamic adjustment of a flaw/defect detection threshold according to claim 1, wherein during said scanning in step (a), at least one transducer is operated to scan test points in said specimen using a pulsed ultrasonic beam such that said pulsed ultrasonic beam intersects a plane of test points being scanned substantially at a 6 dB beam-waist intersection width of said ultrasonic beam.

6. The method for dynamic adjustment of a flaw/defect detection threshold according to claim 1, wherein said calculating step includes dividing a measured signal amplitude for a single test point of said plurality of ultrasonic test data points by a local noise level measured as said rolling average of signal levels proximate said single test point.

7. The method for dynamic adjustment of a flaw/defect detection threshold according to claim 1, wherein during said calculating step said rolling average is calculated using said measurement data acquired from test data points located within a single plane of said distinct points and acquired along at least one segment of said predetermined path scanned by at least one transducer.

8. The method for dynamic adjustment of a flaw/defect detection threshold according to claim 7, wherein said rolling average is calculated using said measurement data acquired, proximate but not adjacent to a test point of said plurality of ultrasonic test data points, along a pair of predetermined scan path segments, a first segment of said pair preceding and separated from said test point by at least one half of a 6 dB beam-waist diameter and a second segment of said pair following and separated from said test point by at least one half of a 6 dB beam-waist diameter, such that a 6 dB beam-waist of an ultrasonic measurement signal pulse will not interfere with said rolling average calculation.

9. The method for dynamic adjustment of a flaw/defect detection threshold according to claim 8, wherein said first and second segments are each three inches in length.

10. The method for dynamic adjustment of a flaw/defect detection threshold according to claim 7, wherein said rolling average is calculated according to the following equation:

$$N_i = \frac{\sum_{j=i-(b/2)-x}^{i-(b/2)} S_j + \sum_{j=i+(b/2)}^{i+(b/2)+x}}{n}$$

where, $N_i$ = local noise level based on rolling average of measured signal levels proximate a test point i,
$S_j$ = signal level at test point j,
b = 6 dB beam width intersection in scan direction,
x = single scan path segment length in inches, and
n = total number of data points in scan path segment pair.

11. The method for dynamic adjustment of a flaw/defect detection threshold according to claim 1, wherein said setting step (c) includes calculating a standard deviation value, $\sigma$, of all said S/N ratio values in said particular plane and defining a flaw/defect detection value for setting said flaw/defect detection threshold for conducting Pitch-Catch type diagnostics as substantially equal to: $1.0 + 2\sigma$.

12. The method for dynamic adjustment of a flaw/defect detection threshold according to claim 1, wherein said setting step (c) includes calculating a standard deviation value, $\sigma$, of all S/N ratio values in said plane and defining a flaw/defect detection value for setting said flaw/defect detection threshold for conducting Axial Long Wave type diagnosis as substantially equal to:

$1.3 \times (1+2\sigma)$ for a Near Field zone, and
$1.1 \times (1+2\sigma)$ elsewhere.

13. The method according to claim 1, wherein a detected flaw/defect is indicated as valid whenever a measured signal level at a test point is equal to or greater than twice said flaw/defect detection threshold set in step (c).

14. The method according to claim 1 wherein said specimen is a turbine rotor forging and wherein said predetermined pattern in said scanning step comprises an arcuate path.

15. The method for dynamic adjustment of a flaw/defect detection threshold according to claim 1, wherein said setting step (c) includes further includes setting a flaw/defect detection threshold for each distinct plane of ultrasonic measurement data acquired in step (a).

16. An automatic flaw/defect indication and dynamic detection threshold adjustment technique for ultrasonic inspection of acoustically noisy materials, comprising the steps of:
 (a) scanning a surface of a specimen under test in a predetermined pattern with at least one transducer and operating said transducer to acquire groups of ultrasonic measurement signal data corresponding to a plurality of ultrasonic test data points arranged within a plane within said specimen;
 (b) calculating a unique signal-to-noise (S/N) ratio value corresponding to each test point in said plane based on a local noise level proximate to each test point wherein said local noise level is computed as a rolling average of ultrasonic measurement signal levels proximate each test data point of measurement data acquired in step (a);
 (c) defining a flaw/defect detection threshold level for said plane based on a predetermined function of a standard deviation value of all S/N values calculated in step (b);
 (d) repeating steps (a) through (c) for each plane inspected within said specimen, whereby said flaw/defect detection threshold level is dynamically reset for each plane;
 (e) indicating a flaw/defect condition at a test point whenever a measured signal level at said test point is substantially equal to or greater than twice said flaw/defect detection threshold set in step (c).

17. The method according to claim 16 wherein said defining step (c) includes calculating a standard deviation value of all S/N ratio values in said plane and defining a flaw/defect detection value, $\sigma$, for setting said threshold for conducting Axial Long Wave type diagnosis as substantially equal to:
$1.3 \times (1+2\sigma)$ for a Near Field zone, and
$1.1 \times (1+2\sigma)$ elsewhere.

18. The method according to claim 16 wherein said defining step (c) includes calculating a standard deviation value, $\sigma$, of all S/N ratio values in said plane and defining a flaw/defect detection value for setting said threshold for conducting Pitch-Catch type diagnostics as substantially equal to: $1.0+2\sigma$.

19. The method according to claim 16 wherein said rolling average is calculated using measurement data acquired, proximate but not adjacent said test point, such that a sonic beam-waist of an ultrasonic measurement signal will not interfere with said rolling average calculation.

20. The method according to claim 16 wherein said specimen is a turbine rotor forging and wherein said predetermined pattern in said scanning step comprises an arcuate path.

* * * * *